(12) United States Patent
Yokosawa et al.

(10) Patent No.: US 11,255,939 B2
(45) Date of Patent: Feb. 22, 2022

(54) MAGNETIC RESONANCE IMAGING APPARATUS, AND AUTOMATIC IMAGING POSITION SETTING METHOD

(71) Applicant: Hitachi, Ltd., Tokyo (JP)

(72) Inventors: Suguru Yokosawa, Tokyo (JP); Toru Shirai, Tokyo (JP); Hisako Nagao, Tokyo (JP); Chikako Moriwake, Tokyo (JP); Binrong Wu, Tokyo (JP)

(73) Assignee: FUJIFILM HEALTHCARE CORPORATION, Chiba (JP)

(*) Notice: Subject to any disclaimer, the term of this patent is extended or adjusted under 35 U.S.C. 154(b) by 0 days.

(21) Appl. No.: 16/889,987

(22) Filed: Jun. 2, 2020

(65) Prior Publication Data
US 2021/0103021 A1    Apr. 8, 2021

(30) Foreign Application Priority Data
Oct. 8, 2019 (JP) .............................. JP2019-185131

(51) Int. Cl.
*G01R 33/56* (2006.01)
*G01R 33/54* (2006.01)
(Continued)

(52) U.S. Cl.
CPC .......... *G01R 33/5608* (2013.01); *A61B 5/055* (2013.01); *A61B 5/107* (2013.01); *G01R 33/546* (2013.01)

(58) Field of Classification Search
CPC .............. G01R 33/5608; G01R 33/546; G01R 33/543; A61B 5/107; A61B 5/055
See application file for complete search history.

(56) References Cited

U.S. PATENT DOCUMENTS 10,514,433 B2    12/2019 Sakurai et al.
2015/0238149 A1*  8/2015 Nitta ..................... A61B 5/7278
                                                            600/413

FOREIGN PATENT DOCUMENTS

JP    2014121598 A    7/2014

OTHER PUBLICATIONS

C. J. den Harder et al., "Consistent automated scan planning of shoulder", Proc. Intl. Soc. Mag. Reson. Med. 16 (2008), pp. 3665.
(Continued)

*Primary Examiner* — Susan S Lee
(74) *Attorney, Agent, or Firm* — Mattingly & Malur, PC

(57) ABSTRACT

A magnetic resonance imaging (MRI) apparatus performs automatic positioning with high accuracy within a short time with respect to tissues having a complicated anatomic structure. First measurement of scout imaging is executed before main imaging for acquiring a diagnosis image, and one-dimensional or two-dimensional measurement data is acquired. The right and left of a subject is determined by using the measurement data acquired in the first measurement. A cross-section position in second measurement of the scout imaging is calculated by using a determination result in the right and left determination and the measurement data acquired in the first measurement, the second measurement at the cross-section position is executed, and two-dimensional measurement data is acquired. A cross-section position in the main imaging is calculated by using the two-dimensional measurement data acquired in the second measurement.

17 Claims, 17 Drawing Sheets

(51) Int. Cl.
*A61B 5/107* (2006.01)
*A61B 5/055* (2006.01)

(56) References Cited

OTHER PUBLICATIONS

Yiqiang Zhang et al., "Roubst Automatic Knee MR Slice Positioning Through Redundant and Hierarchical Anatomy Detection", IEEE Transactions on Medical Imaging, vol. 30, No. 12, Dec. 2011, pp. 2087-2100.

* cited by examiner

FIRST SCOUT
AX IMAGE

SECOND SCOUT
IMAGING POSITION

PARTIALLY ENLARGED
VIEW OF FIG. 9A

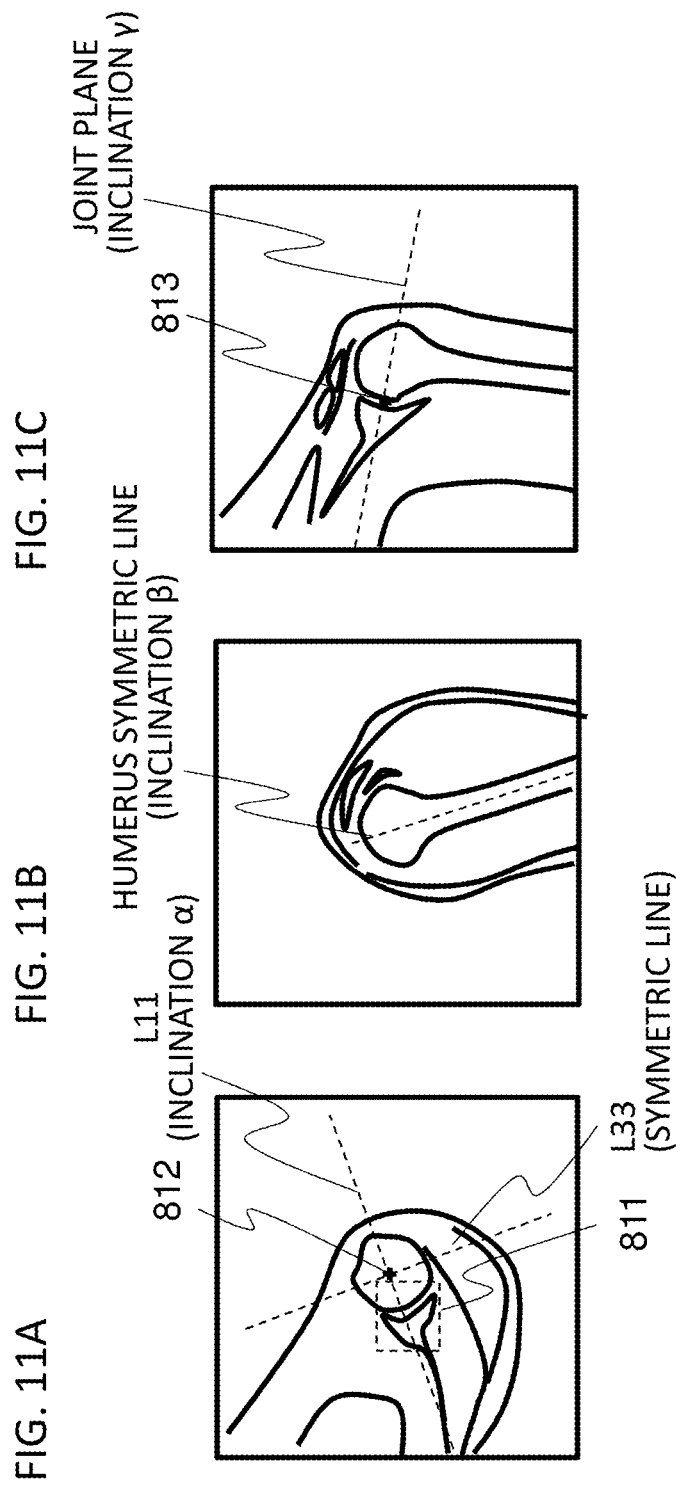

FIG. 12A AX PLANE IMAGING POSITION
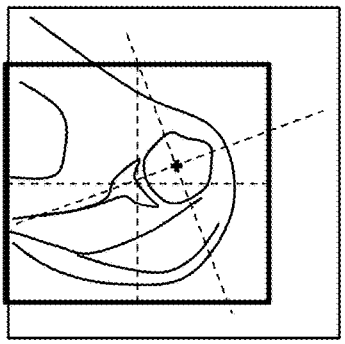
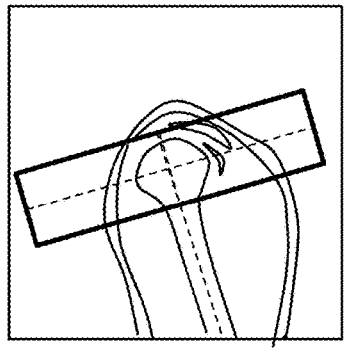
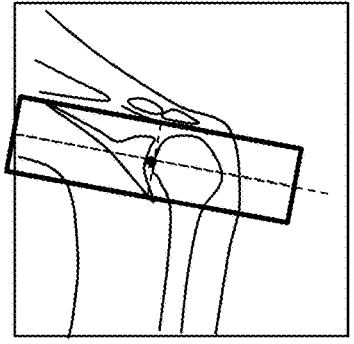
FIG. 12B SAG PLANE IMAGING POSITION
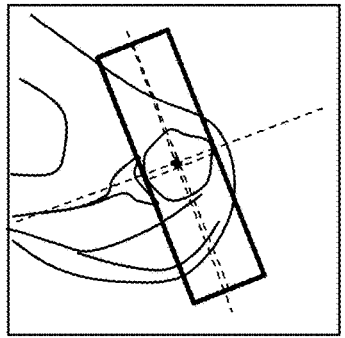
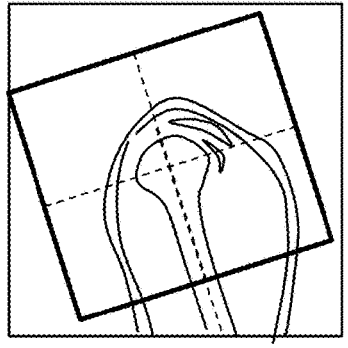
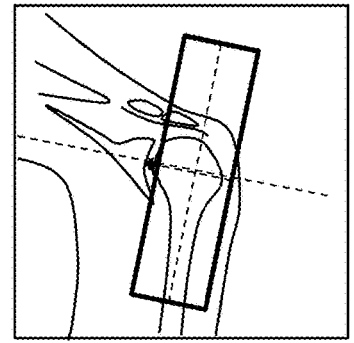
FIG. 12C COR PLANE IMAGING POSITION
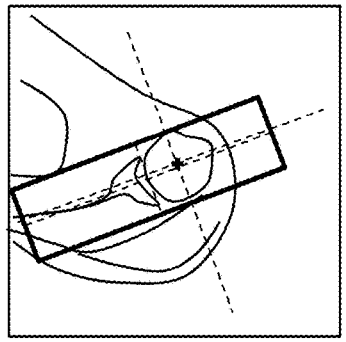
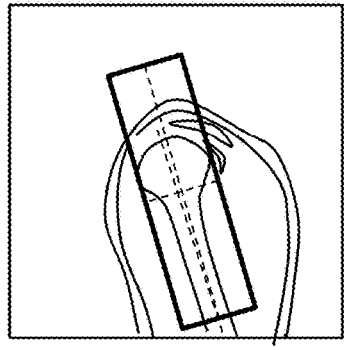
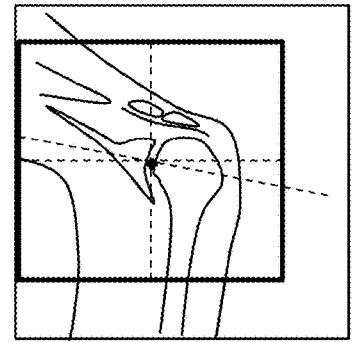

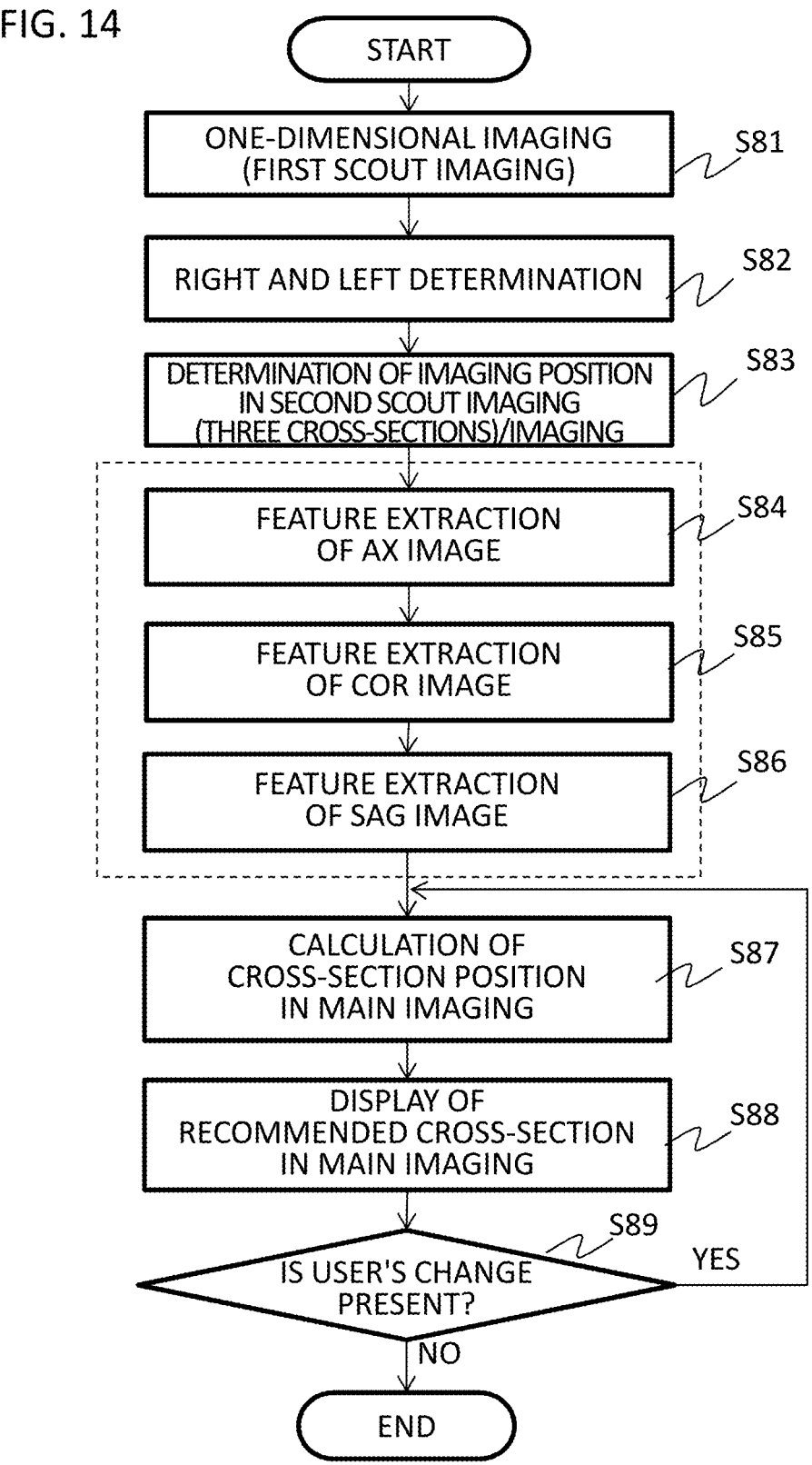

FIG. 16A AX PLANE IMAGING POSITION
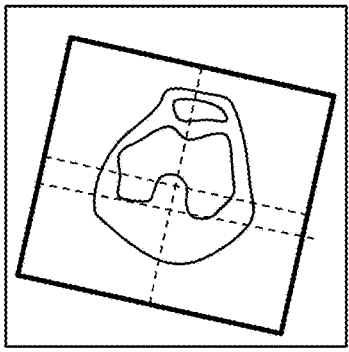 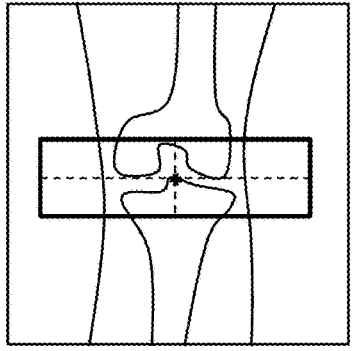 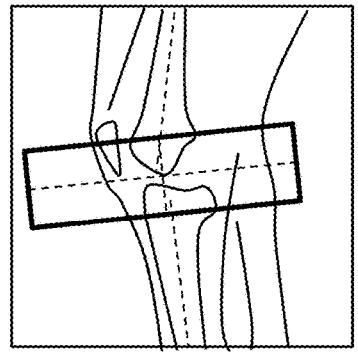
FIG. 16B SAG PLANE IMAGING POSITION
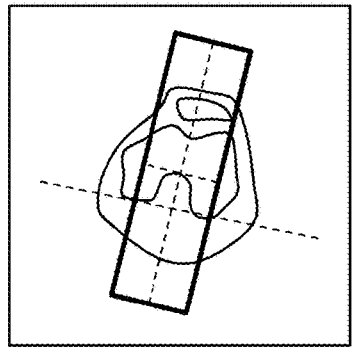 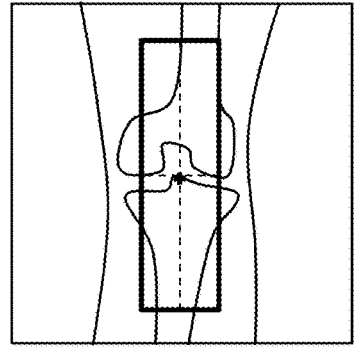 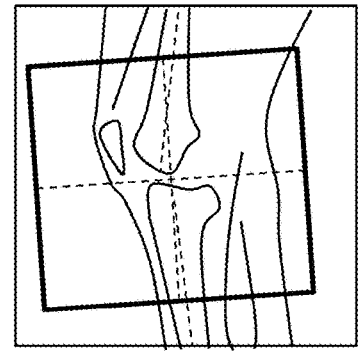
FIG. 16C COR PLANE IMAGING POSITION
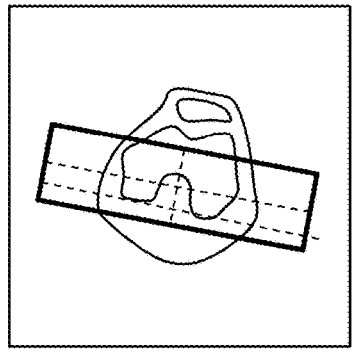 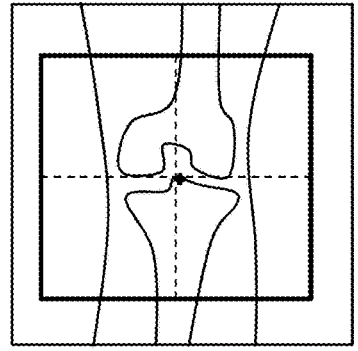 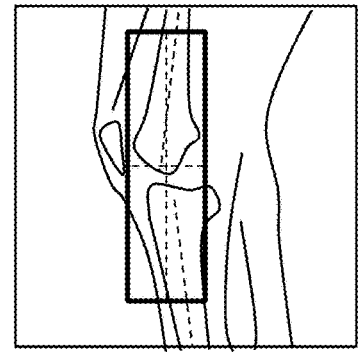

MAGNETIC RESONANCE IMAGING APPARATUS, AND AUTOMATIC IMAGING POSITION SETTING METHOD

INCORPORATION BY REFERENCE

The present application claims priority from Japanese patent application JP-2019-185131 filed on Oct. 8, 2019, the content of which is hereby incorporated by reference into this application.

BACKGROUND OF THE INVENTION

Field of the Invention

The present invention relates to a magnetic resonance imaging apparatus (hereinafter, referred to as "MRI apparatus"), and particularly to, a technology of automatically setting an imaging position.

Description of the Related Art

The MRI apparatus can image a cross-section of a subject in an arbitrary direction, and thus a cross-section image suitable for diagnosis can be obtained. In general, in the case of setting an imaging cross-section in the MRI, first, images of three orthogonal cross-sections of axial, coronal, and sagittal are acquired as a positioning image (also referred to as "scout image") for positioning, and an imaging position is determined by setting an anatomic tissue set as a mark on the scout image. In the related art, determination of the imaging position is performed through a manual operation through a user interface, but a function (referred to as "automatic positioning function") of automatically presenting the imaging position through image processing of the scout image has been developed (for example, refer to JP-A-2014-121598).

With regard to determination of an imaging cross-section by the automatic positioning function, in a case where a feature of the anatomic tissue shown on the scout image can be extracted through image processing in a relatively easy manner, the determination can be performed with accuracy. However, in a joint such as a shoulder and a knee which have a complicated three-dimensional structure, it is difficult to identify the anatomic tissue as a mark of the imaging position only by the scout image acquired once. Therefore, a position of a second scout image is determined from the first scout image, and an imaging position of a diagnosis image is determined with the second scout image.

The imaging position determined is presented by a display device or the like in order for a user to confirm the imaging position. At this time, it is necessary for the user to determine whether or not the presented imaging position is acceptable, and thus the imaging position is presented on a cross-section where an anatomic tissue serving as a mark when determining the imaging position can be identified. For example, in shoulder examination, as an image for presenting the imaging position, an axial plane image capable of identifying a scapula and a humerus, an oblique sagittal plane image capable of identifying an inclination of the humerus, and an oblique coronal plane image capable of identifying a joint surface of the scapula and the humerus are necessary.

With respect to the demand, there are suggested a technology of acquiring a three-dimensional scout image, detecting a mark by an algorithm of a model base using a 3D deformable mesh adaption, and automatically positioning an imaging cross-section in MR examination of a shoulder joint (C. J. den Harder etc., "Consistent automated scan planning of shoulder" Proc. Intl. Soc. Mag. Reson. Med. 19 (2008), p 3665), and a technology of acquiring a three-dimensional scout image, detecting a positional relationship between a plurality of different anatomic structures of a plurality of sites to reduce erroneous detection, and performing hierarchical learning for extracting invariance of the anatomic structures to reduce an error caused by a difference in a direction and bending of an individual knee, or the like in examination of a knee joint (Yiqiang Zhan, "Robust Automatic Knee MR Slice Positioning Through Redundant and Hierarchical Anatomy Detection").

In the technologies of the related art as described above, the three-dimensional scout image is acquired to raise automatic positioning accuracy with respect to tissues having a complicated anatomic structure, but long imaging time is taken in three-dimensional imaging, and a lot of pieces of information which are not necessary for specifying an imaging cross-section are included in the three-dimensional scout image. That is, excessive information is acquired.

In addition, after presenting a determined imaging cross-section, in a case where the imaging cross-section is determined as inappropriate, it takes time to correct the imaging cross-section, and it may be necessary to perform long-time three-dimensional imaging again.

SUMMARY OF THE INVENTION

Here, an object of the invention is to provide a technology capable of realizing automatic positioning with high accuracy within a short time with respect to tissues having a complicated anatomic structure.

According to the invention, a focus is given to a situation in which processing required when automating a cross-section of a complicated tissue includes processing of determining the right and left and processing of extracting an anatomic feature, and information necessary for the processing and the amount of information are different in each case. With respect to processing that is performed with less information, measurement capable of acquiring the information within a short time is performed, thereby raising acquisition efficiency of information to be measured and shortening automatic positioning time while maintaining accuracy.

That is, according to an aspect of the invention, there is provide an MRI apparatus including: an imaging unit that acquires a cross-section image of a subject by using nuclear magnetic resonance; an imaging control unit that performs control so that the imaging unit performs scout imaging for acquiring a scout image used for determining an imaging position, and main imaging for acquiring a diagnosis image; and an imaging cross-section determination unit that determines an imaging cross-section position of the main imaging by using data acquired in the scout imaging. The imaging control unit performs control of executing first measurement for acquiring one-dimensional or two-dimensional measurement data and second measurement for acquiring two-dimensional measurement data as the scout imaging. The imaging cross-section determination unit includes a right and left determination unit that determines the right and left of the subject by using the measurement data acquired in the first measurement, and a cross-section position calculation unit that calculates a cross-section position in the second measurement by using a determination result in the right and left determination and the measurement data acquired in the first measurement, and calculates a cross-section position in the main imaging by using the measurement data acquired in the second measurement.

In addition, according to another aspect of the invention, there is provided an automatic imaging position setting method (automatic positioning method) in an MRI device. The method includes: executing first measurement of scout imaging and acquiring one-dimensional or two-dimensional measurement data before main imaging for acquiring a diagnosis image; determining the right and left of a subject by using measurement data acquired in the first measurement; calculating a cross-section position in second measurement of the scout imaging by using a determination result in the right and left determination and the measurement data acquired in the first measurement, executing the second measurement at the cross-section position, and acquiring two-dimensional measurement data; and calculating a cross-section position in the main imaging by using the two-dimensional measurement data acquired in the second measurement.

According to the invention, the right and left determination which is a premise in feature extraction of a completed tissue is performed with the one-dimensional or two-dimensional measurement data, and thus acquisition of redundant measurement data becomes unnecessary, and an imaging time as a whole can be shortened. In addition, the cross-section position in the subsequent scout imaging is calculated on the basis of the right and left determination, and thus it is possible to obtain accurate information necessary for setting the imaging cross-section position from the two-dimensional scout image. As a result, it is possible to perform automatic positioning within a short time while maintaining the same accuracy as in the case of acquiring three-dimensional data.

BRIEF DESCRIPTION OF THE DRAWINGS

FIG. 7A illustrates an axial image of a shoulder which is two-dimensional data, and FIG. 7B illustrates one-dimensional projection of the image in FIG. 7A;

FIG. 9A illustrates matching processing, FIG. 9B is an enlarged view of a main portion, and FIG. 9C illustrates an imaging cross-section position determined after feature extraction;

FIGS. 11A to 11C are views illustrating processing of the feature extraction unit with respect to a second scout image and an MPR image, FIG. 11A illustrates a scout AX image, FIG. 11B illustrates a SAG image after the MPR processing, and FIG. 11C illustrates a COR image after the MPR processing;

FIGS. 12A to 12C are views illustrating a presentation example of an imaging cross-section position in main imaging, FIG. 12A illustrates an AX plane, FIG. 12B illustrates a SAG plane, and FIG. 12C illustrates a COR plane;

FIG. 14 is a flowchart illustrating an example of an automatic positioning procedure of a second embodiment;

FIG. 15A illustrates a scout AX image, FIG. 15B illustrates a SAG image after the MPR processing, and FIG. 15C illustrates a COR image after the MPR processing; and FIGS. 16A to 16C are views illustrating a presentation example of an imaging cross-section position in main imaging, FIG. 16A illustrates an AX plane, FIG. 16B illustrates a SAG plane, and FIG. 16C illustrates a COR plane.

DETAILED DESCRIPTION OF THE INVENTION

Hereinafter, embodiments of an MRI apparatus of the invention will be described with reference to accompanying drawings.

Figure 1:
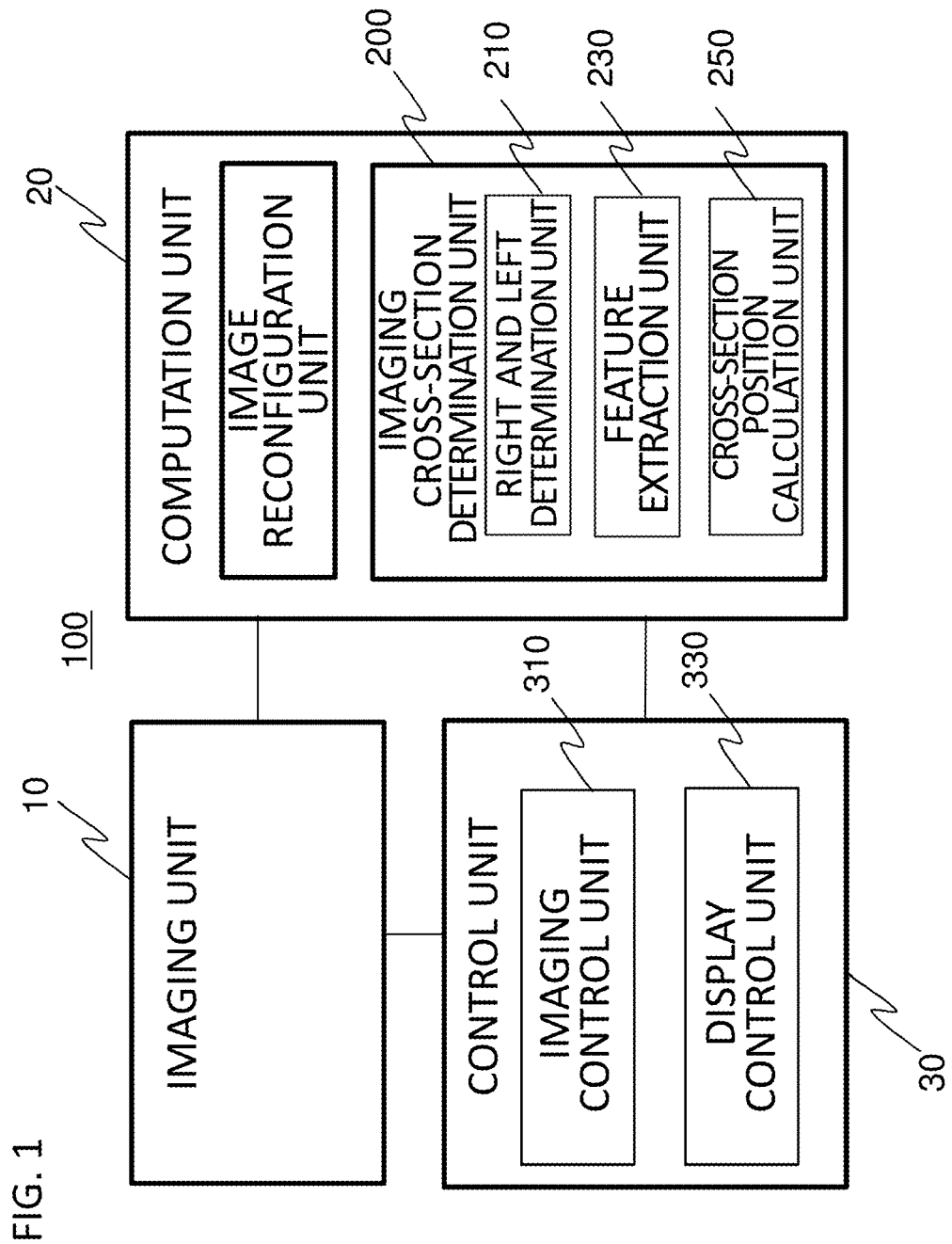
FIG. 1 is a block diagram illustrating an overall configuration of an embodiment of an MRI apparatus of the invention.

As illustrated in FIG. 1, an MRI apparatus 100 includes an imaging unit 10 that acquires a cross-section image of a subject by using nuclear magnetic resonance, a computation unit 20 that performs various kinds of computation with respect to an image acquired by the imaging unit 10, and a control unit 30 that controls an operation of the imaging unit 10 or the computation unit 20.

Figure 2:
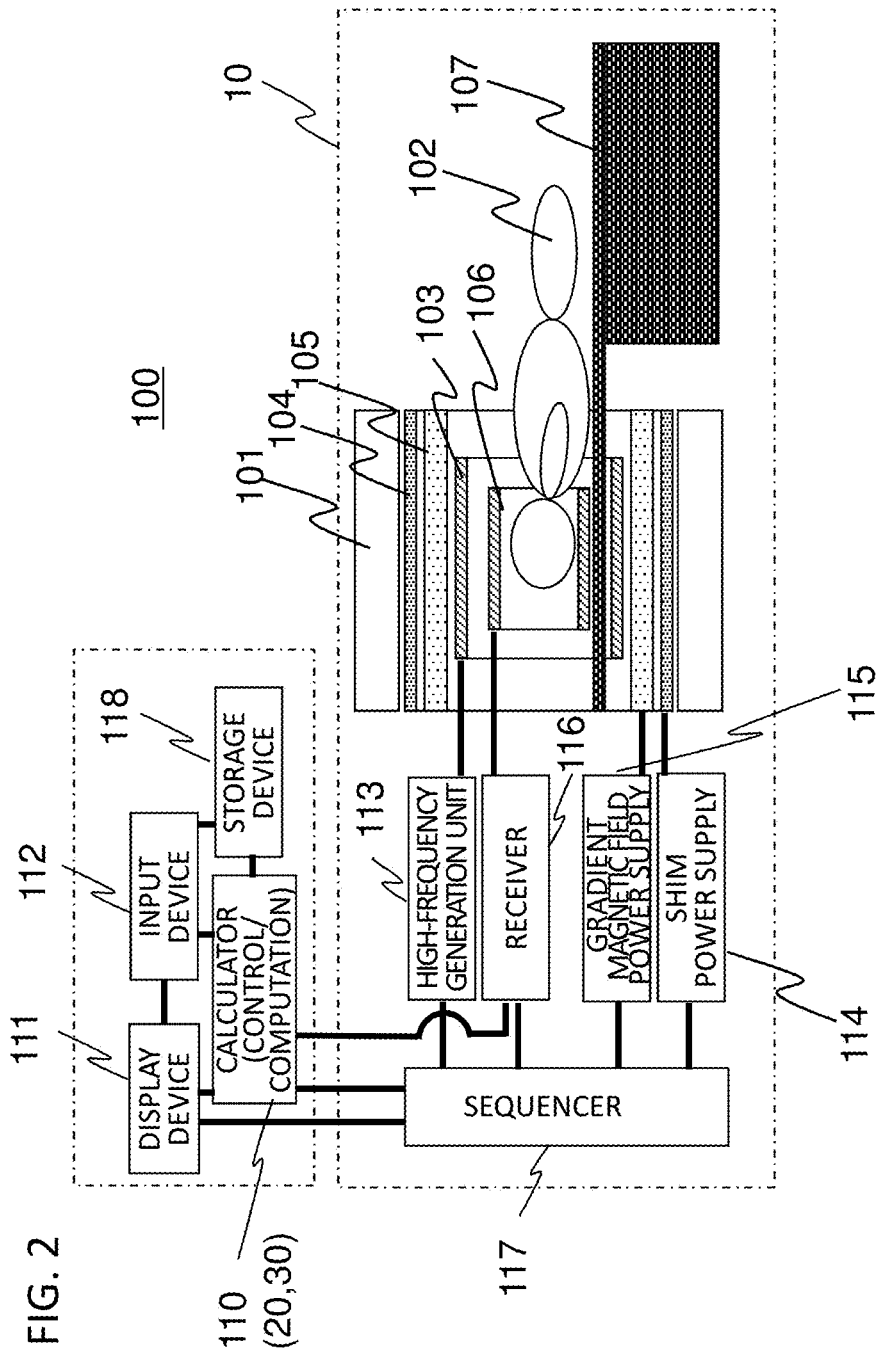
FIG. 2 is a block diagram illustrating an example of the MRI apparatus to which the invention is applied.

A configuration of the imaging unit 10 is similar to a configuration of an imaging unit of a known MRI apparatus. Specifically, as illustrated in FIG. 2, the MRI apparatus 100 includes a static magnetic field magnet 101 that generates a static magnetic field in a space in which a subject (examination site) 102 is disposed, a transmission RF coil 103 that applies a high-frequency magnetic field with respect to the subject 102, a shim coil 104 configured to increase uniformity of the static magnetic field, a gradient magnetic field coil 105 that generates gradient magnetic fields in three axial directions in the static magnetic field space, a reception RF coil 106 that detects a nuclear magnetic resonance signal (high-frequency signal) generated from the subject 102, and the like as an imaging unit. In addition, a bed 107 for disposing the subject 102 in the static magnetic field space is provided.

The transmission RF coil 103 is connected to a high-frequency generation unit 113 that generates a high-frequency signal, the shim coil 104 is connected to a shim power supply 114, and the gradient magnetic field coil 105 is connected to a gradient magnetic field power supply 115, respectively. In addition, the reception RF coil 106 is connected to a receiver 116 that performs detection of a nuclear magnetic resonance signal and conversion into a digital signal, and the like. The high-frequency generation unit 113, the shim power supply 114, the gradient magnetic field power supply 115, and the receiver 116 operate by a control signal transmitted from a sequencer 117 that operates on the basis of a command of a calculator 110. The calculator 110 is provided with an input device 112 such as a display (display device) 111, a mouse, and a keyboard, a storage device 118, and the like as an auxiliary device, reads out a pulse sequence that determines in advance a pulse shape and an application timing of the gradient magnetic field or the high-frequency pulse, and the like from the storage device 118, and sets imaging conditions (an imaging cross-section, echo time, repetition time, and the number of times of repetition) and the like which are set by a user in the sequencer 117 through the input device 112. According to this, predetermined imaging or measurement is executed by the imaging unit 10. With regard to a direction of the imaging cross-section, a phase encode direction, a slice direction, and a read-out direction are determined in accordance with a combination of the gradient magnetic fields in three axial directions, and three cross-sections (for example, an axial plane, a coronal plane, and a sagittal plane) of which axial directions are the directions and are orthogonal to each other are determined.

Imaging executed by the imaging unit 10 includes positioning imaging (referred to as "scout imaging") for determining a cross-section position (imaging position) in imaging in addition to imaging (main imaging) for acquiring a diagnosis image, and the scout imaging includes two kinds of measurement, that is, first measurement (first scout imaging) for collecting data necessary to determine the right and left of an examination target, and second measurement (second scout imaging) for collecting data necessary for extracting a feature of a tissue or a site (collectively referred to as "tissue") of the examination target.

Computation performed by the computation unit 20 includes various kinds of computation. In the MRI apparatus of this embodiment, the computation unit 20 includes an imaging cross-section determination unit 200 that determines an imaging cross-section for image acquisition by using measurement data acquired in the positioning imaging, and the imaging cross-section determination unit 200 includes a right and left determination unit 210 that determines the right and left of the examination target by using the data (the first measurement data) acquired in the first scout imaging, a feature extraction unit 230 that performs feature extraction for the examination target site by using the data acquired in the scout imaging, and a cross-section position calculation unit 250 that calculates an imaging cross-section position in the second scout imaging and the main imaging to be subsequently performed.

The control unit 30 includes an imaging control unit 310 that controls the imaging unit 10 in accordance with a predetermined examination protocol (that determines the kind of an imaging sequence, an execution procedure thereof, or the like in correspondence with an examination target) or a user's setting or command, and a display control unit 330 that performs presentation of a computation result obtained by the computation unit 20, reception of the user's setting through a user interface, or the like. In a case where an examination target of the examination protocol is a tissue such as a knee joint and a shoulder joint which have a complicated structure, the imaging control unit 310 causes the imaging unit 10 to execute scout imaging twice as the positioning imaging. In addition, in a case where an imaging cross-section presented by the imaging cross-section determination unit 200 by using a result of the second scout imaging is approved by a user, the imaging unit 10 is caused to execute the main imaging at the cross-section.

The functions of the computation unit 20 and the control unit 30 can be realized by executing a predetermined program in a central processing unit (CPU) of the same or individual calculator. In addition, a part of the function of the computation unit 20 may be realized by hardware such as an application specific integrated circuit (ASIC) or afield programmable gate array (FPGA). In the configuration illustrated in FIG. 2, the calculator 110 realizes the function.

When the examination target is specified, the MRI apparatus of this embodiment automatically performs the positioning imaging for determining the imaging cross-section of the examination target in accordance with a predetermined procedure, determines the imaging cross-section in the main imaging, and presents a user with the imaging cross-section in the main imaging.

Figure 3:
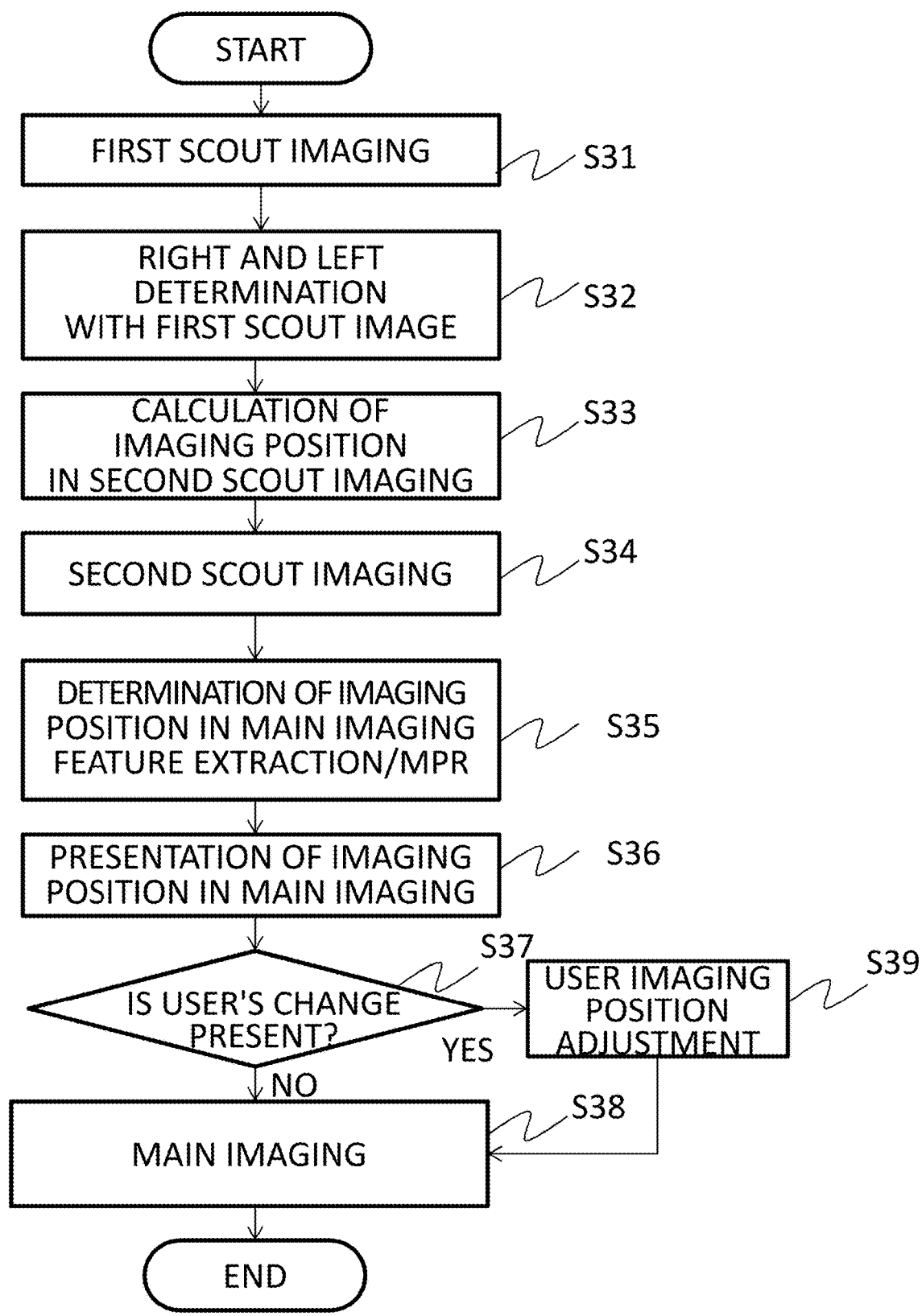
FIG. 3 is a flowchart illustrating an overview of an automatic positioning procedure.

Hereinafter, a flow of imaging cross-section determination processing according to this embodiment will be described with reference to FIG. 3.

First, the reception RF coil 106 is mounted at the periphery of an examination site of the subject 102, and the subject 102 is placed in the static magnetic field space. The imaging control unit 310 controls the imaging unit 10, executes the first scout imaging, and acquires the first measurement data (S31). For example, the first scout imaging is measurement for collecting an echo signal while applying a read-out gradient magnetic field after irradiation with an RF pulse which is performed once, and when the echo signal is subjected to one-dimensional fourier transformation, one-dimensional data indicating signal intensity (a projection value in an axial direction) in a read-out direction is obtained. At this time, it is preferable that the read-out direction (for example, the direction is assumed as an X-direction) approximately matches a right and left direction of the subject 102. For example, the second measurement measures an echo signal having a small number of phase encodes. When the echo signal is subjected to two-dimensional fourier transformation, two-dimensional image data is obtained as second measurement data. In the measurement, the read-out direction may not match the right and left direction of the subject.

The imaging cross-section determination unit 200 receives the first measurement data from the imaging unit 10, and the right and left determination unit 210 determines the right and left of an image on the basis of signal intensity of the read-out direction which is obtained from the first measurement data (S32). Next, the cross-section position calculation unit 250 calculates an imaging cross-section position in the second scout imaging on the basis of a determination result of the right and left determination unit 210 (S33). In the second scout imaging, an axial plane image (AX image), a coronal plane image (COR image), and a sagittal plane image (SAG image) are acquired, and thus imaging positions are respectively calculated with respect to the three cross-sections.

Specifically, in a case where the first measurement data is the one-dimensional data, a cross-section position of one cross-section in the second scout imaging, for example, the AX plane is determined on the basis of a right and left determination result. In addition, features (a position, an inclination, a shape, and the like) of an examination target site are extracted from the two-dimensional data (for example, the AX image) acquired at the cross-section position, and a position or an inclination (an oblique plane) of the other cross-sections (the SAG plane and the COR plane) is determined on the basis of the features. In addition, for example, in a case where the first measurement data is two-dimensional data of one cross-section (the AX plane), the right and left determination is performed by using the two-dimensional data, and cross-section positions of a plurality of cross-sections including the one cross-section in the second scout imaging are determined by using the features of the examination target portion which are extracted from the two-dimensional image data.

When the imaging cross-section position in the second scout imaging is determined, the imaging control unit 310 controls the imaging unit 10 to perform the second scout imaging under a gradient magnetic application condition corresponding to the position that is determined (S34). In the second scout imaging, imaging for obtaining a two-dimensional image is performed by setting an AX image of a predetermined position, an oblique SAG image according to a structure of a tissue, and an oblique COR image as an imaging cross-section. Typically, in imaging of each cross-section, images of a plurality of parallel planes (a plurality of pieces of slice data) are acquired. Particularly, with regard to the sagittal plane and the coronal plane, a plurality of pieces of slice data are acquired to subsequently perform multi-planar reconstruction (MPR) processing.

Figure 4:
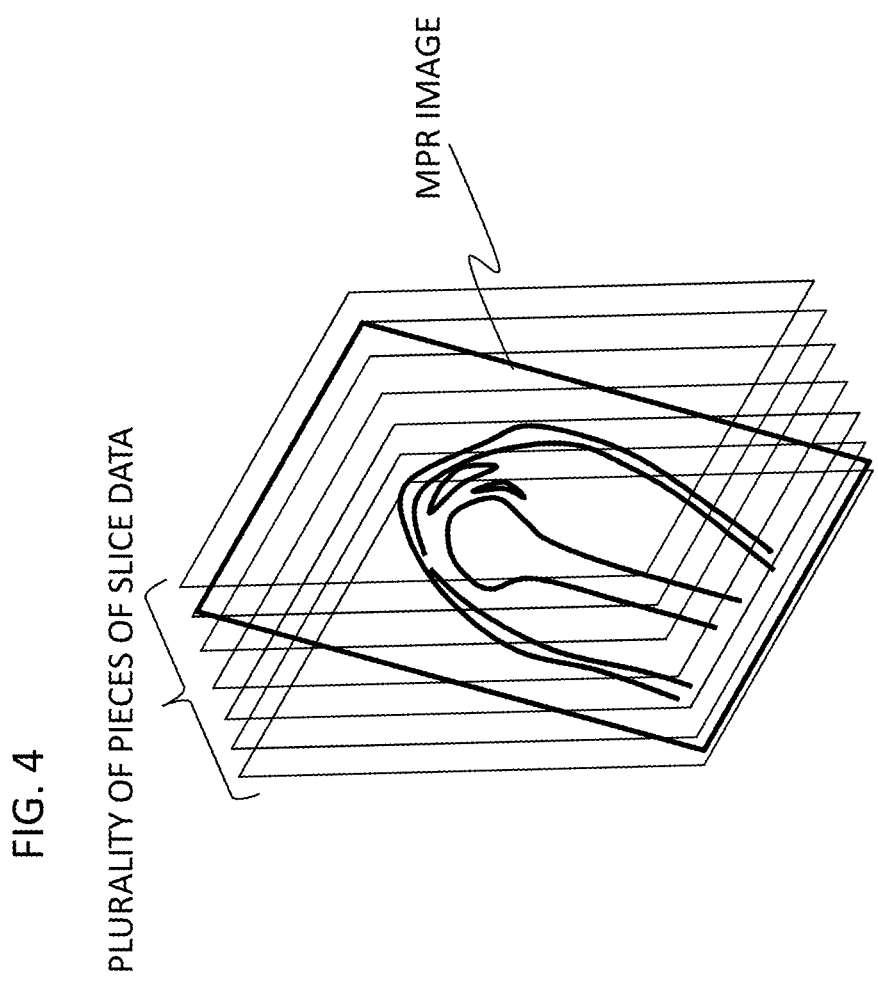
FIG. 4 is a view illustrating MPR processing.

The imaging cross-section determination unit 200 receives image data (second measurement data) of the second scout imaging from the imaging unit 10, and determines an imaging cross-section of the main imaging (S35). Accordingly, first, the feature extraction unit 230 extracts features of an examination target tissue from a plurality of images included in the second measurement data, and calculates a position of the tissue to be the center of an image, and an inclination of the tissue for cutting out an image from a plurality of sagittal plane images and a plurality of coronal plane images. On the basis of the information, the MPR processing is performed with respect to the plurality of sagittal plane images and the plurality of coronal plane images to determine a plane (cut-out plane) in which features are included. As illustrated in FIG. 4, for example, the plane is a plane cut-out from the plurality of sagittal plane images, and an oblique plane having a predetermined inclination with respect to a sagittal plane. Next, an inclination is calculated by using the features of the examination target tissue in the cut-out plane. With regard to the coronal plane, an inclination is calculated by using the features of the examination target tissue. The imaging cross-section in the main imaging is determined on the basis of the inclination and the position of the examination target tissue which are obtained by the above-described processing, for example, so that a predetermined position becomes the center of an image and is parallel to the inclination of the examination target tissue.

When the imaging cross-section determination unit 200 determines three cross-sections, the display control unit 330 receives the information, and presents the information to a user (S36). With regard to a method of presenting the information to the user, for example, a screen in which a recommended imaging cross-section position is superimposed on images of the three cross-sections is displayed on a display. For example, a user interface for inputting a user's instruction or a user's adjustment as to whether or not to initiate the main imaging on the recommended imaging cross-section may be displayed on the same screen. In a case where the user inputs initiation of the main imaging (S37), the main imaging is initiated (S38). In the case of the user's adjustment, a change of the presented imaging cross-section position is received (S39), and the main imaging is initiated after the user's adjustment. As a display aspect of the display or the user interface, various aspects can be employed, and several examples will be described in detail in the following embodiment.

According to the MRI apparatus of this embodiment, since the right and left determination which is a premise in automatic positioning is performed by one-dimensional measurement or two-dimensional measurement, and data necessary for determining main imaging cross-section position is acquired by two-dimensional measurement by using the result, it is possible to greatly reduce time taken for scout imaging including the second scout imaging. In addition, since the second scout imaging is performed on the basis of the right and left determination result, it is possible to improve accuracy of feature extraction in an image obtained in the scout imaging that is the two-dimensional measurement, and imaging position calculation based on the feature extraction.

Hereinafter, with regard to a specific examination site, description will be given of an embodiment to which an automatic positioning technology of the invention is applied.

First Embodiment

Figure 5:
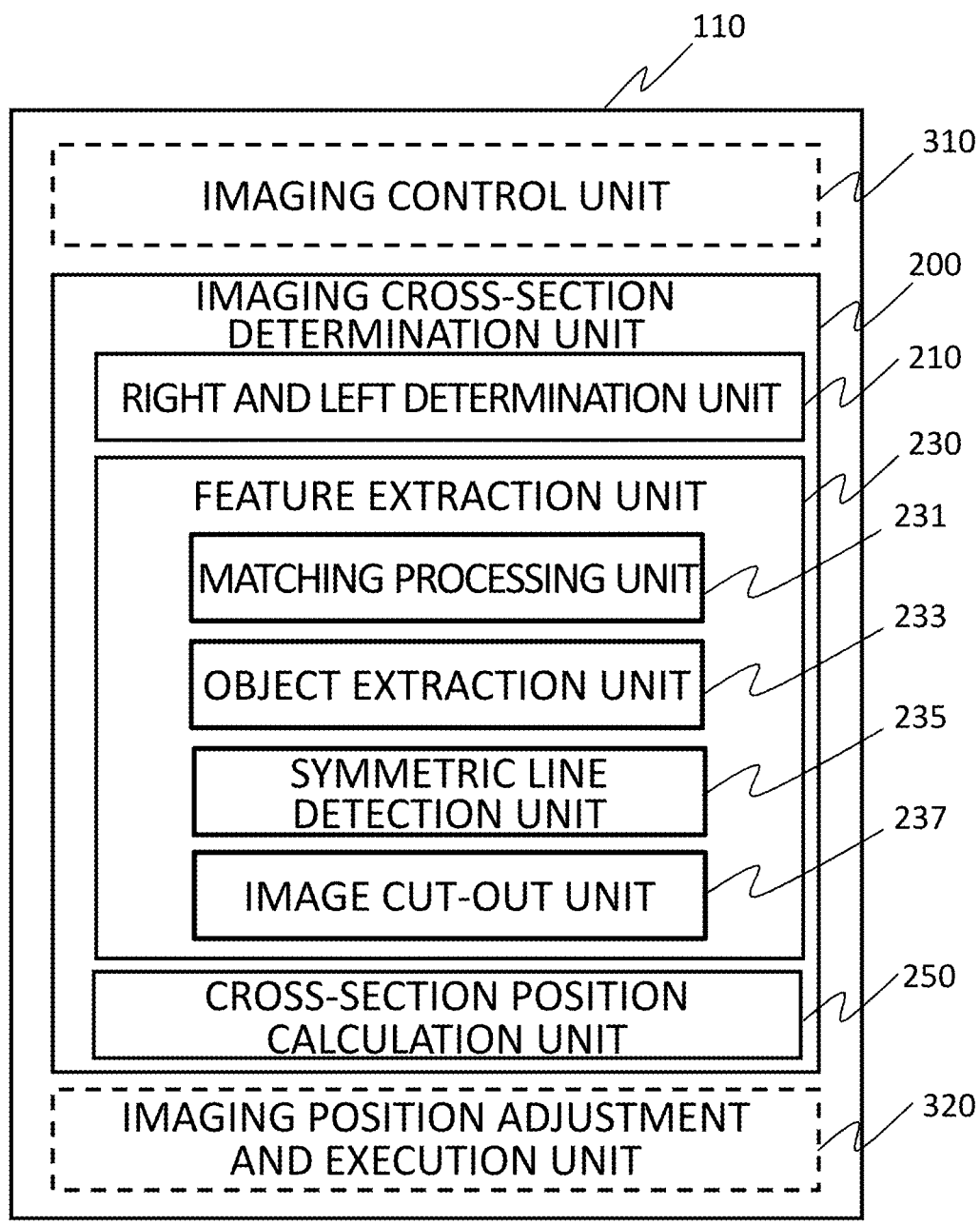
FIG. 5 is a functional block diagram of a calculator that executes an automatic positioning function of a first embodiment.

This embodiment is an embodiment of automatic positioning processing in a case where the examination site is a shoulder joint. Here, description will be given of the case of automatically setting three cross-sections including a humerus with focus given to the shoulder joint as an imaging cross-section, Even in this embodiment, a configuration of an apparatus is similar to the configuration illustrated in FIG. 1 and FIG. 2, and a flow of basic processing is similar to FIG. 3. A detailed configuration relating to automatic positioning of the calculator 110 (the computation unit 20 and the control unit 30) in this embodiment is illustrated in FIG. 5. In FIG. 5, the same reference numeral will be given of the same element as the element illustrated in FIG. 1, and redundant description will be omitted.

As illustrated in FIG. 5, the feature extraction unit 230 of the imaging cross-section determination unit 200 includes a matching processing unit 231 that performs processing of identifying a specific tissue, an object extraction unit 233 that extracts a specific tissue, a symmetric line detection unit 235 that detects a lateral symmetric line with respect to an object that is extracted, and an image cut-out unit 237 that cuts out a sheet of image (MPR image) from a plurality of pieces of slice data by MPR processing. In addition, as a function of the control unit 30, an imaging position adjustment and execution unit 320 that receives, via the display device 111, a user's change relating to an imaging cross-section position, and executes the change content is provided.

Figure 6A:
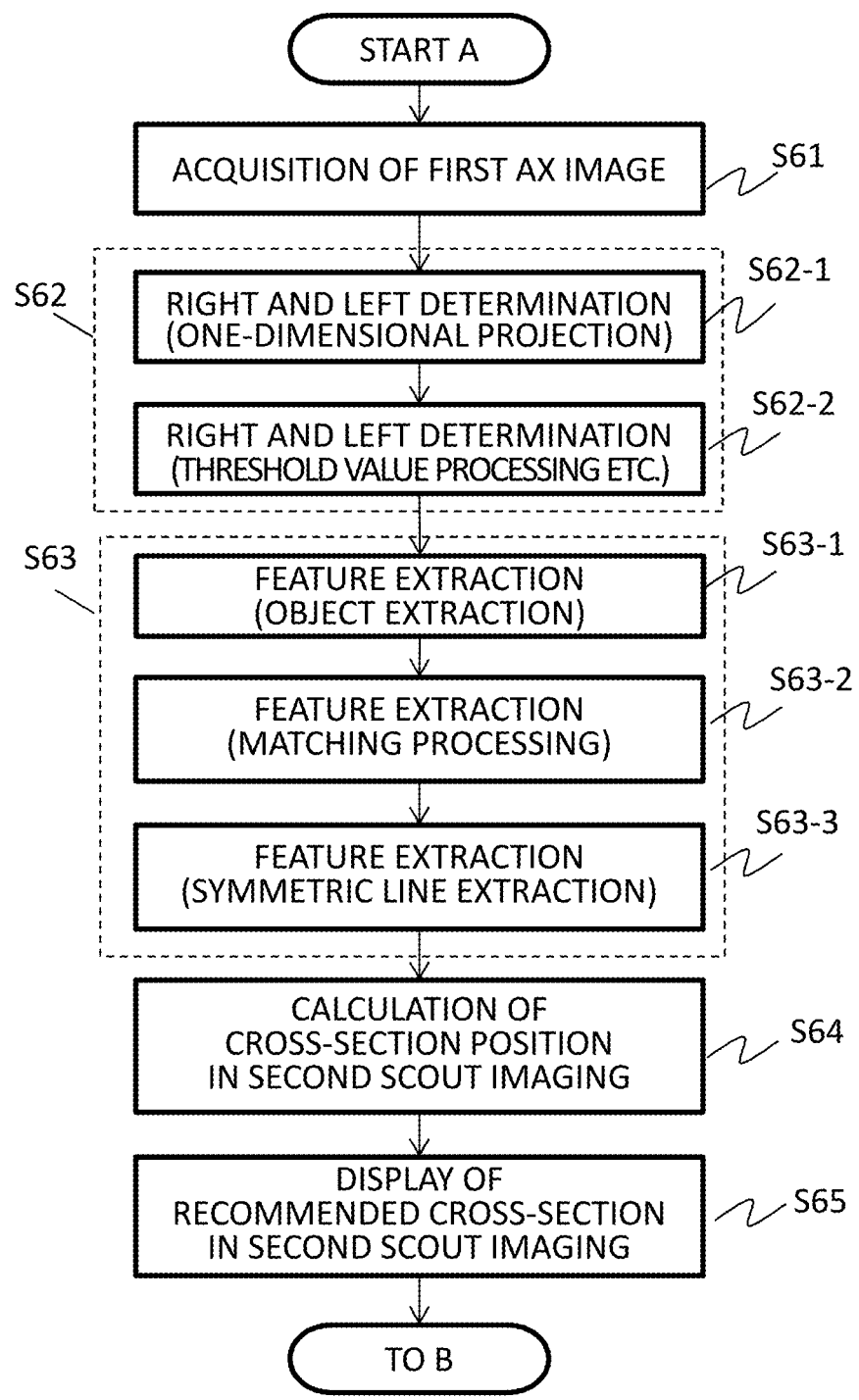
FIG. 6A is a flowchart illustrating an example of an automatic positioning procedure of the first embodiment, and illustrates a flow up to second scout imaging cross-section position determination.
Figure 6B:
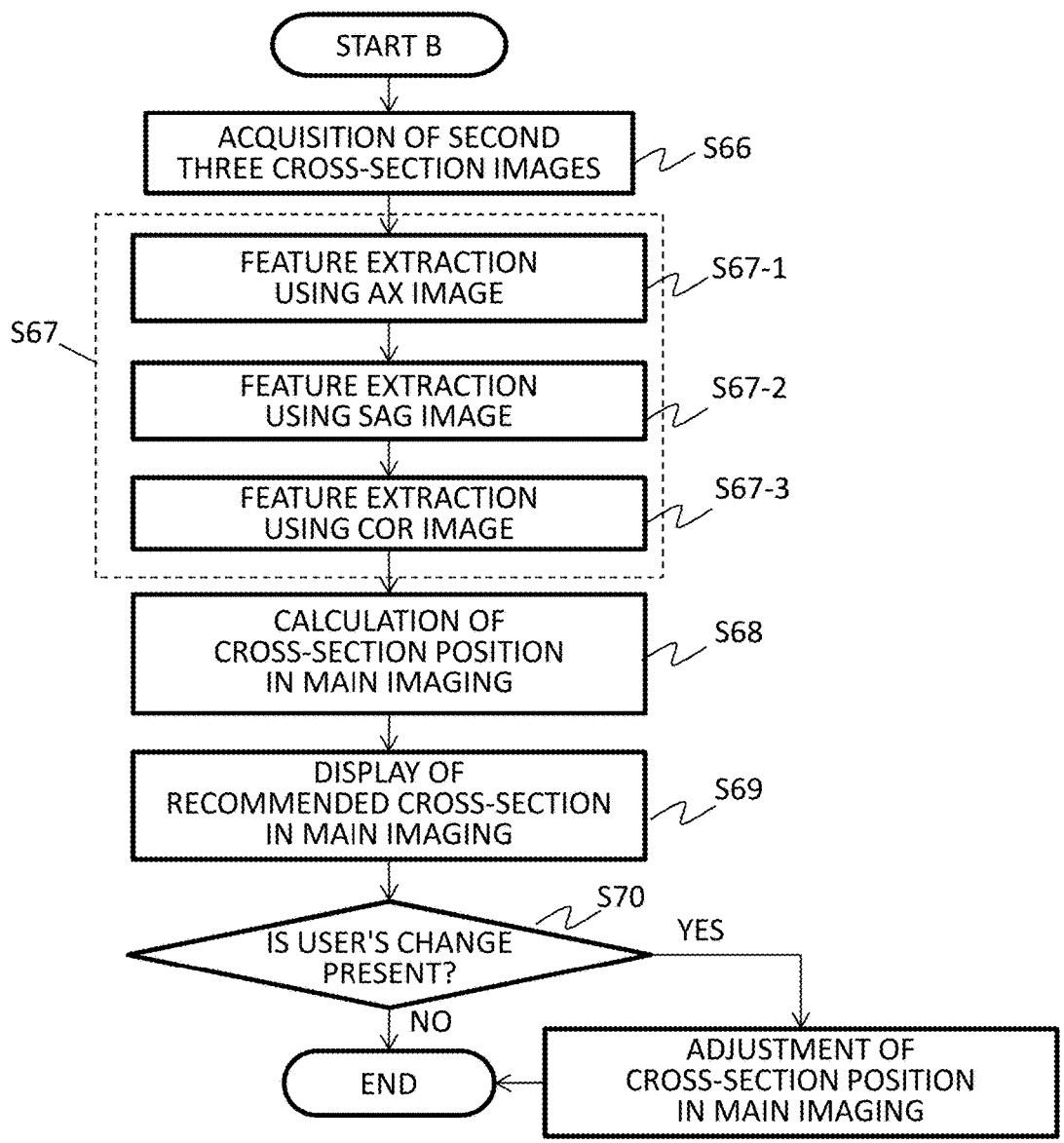
FIG. 6B is a flowchart illustrating an example of the automatic positioning procedure of the first embodiment, and illustrates a flow up to determination of cross-section position in main imaging.

Imaging cross-section determination processing in this embodiment will be described with reference to FIGS. 6A and 6B with focus given to processing of each unit of the imaging cross-section determination unit 200. FIGS. 6A and 6B are views illustrating a processing flow. FIG. 6A illustrates a flow from first scout imaging to imaging position determination for second scout imaging, and FIG. 6B illustrates a flow from the second scout imaging to imaging position determination for main imaging.

<S61: First Scout Imaging>

Under the control of the imaging control unit 310, the imaging unit 10 executes first scout imaging, and acquires a scout image. In this embodiment, it is assumed that two-dimensional imaging is performed by selecting a target region, and an AX image of one or a plurality of slices is acquired.

<S62: Right and Left Determination Processing>

<<S62-1: One-Dimensional Projection Image Creation>>

The right and left determination unit 210 sets the AX image acquired in the scout imaging as an input, and creates a one-dimensional projection image projected on an X-axis corresponding to a right and left axis of a body axis. In a case where the AX image includes a plurality of pieces of slice data, one-dimensional projection images obtained by projecting the plurality of pieces of slice data on the X-axis are added to form a one-dimensional projection image for right and left determination.

<<S62-2: Right and Left Determination>>

Figure 7A:
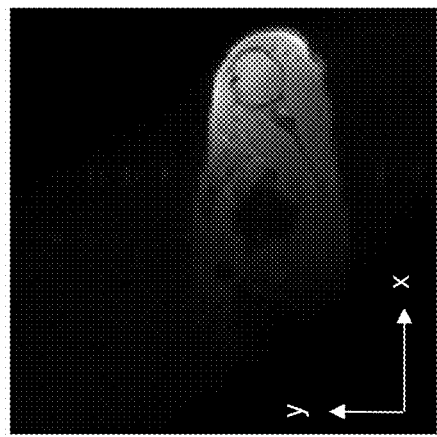
FIGS. 7A and 7B are views illustrating measurement data obtained in the first scout imaging.
Figure 7B:
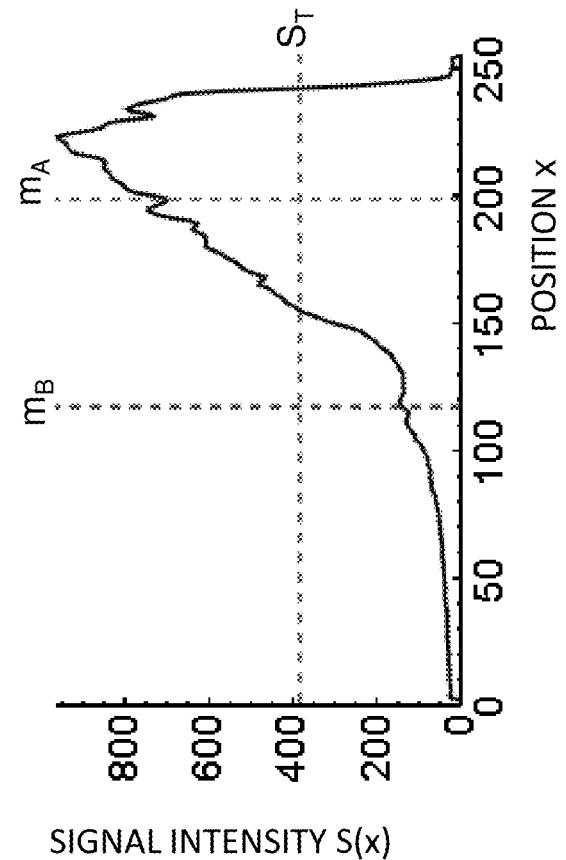

Next, the right and left determination unit 210 determines whether an examination site is a right shoulder or a left shoulder from the one-dimensional projection image. For example, in the case of examining the right shoulder joint, the reception RF coil is mounted on the right shoulder, and in an image acquired in that state, a signal value from the right shoulder is high, and a signal value from the other regions is low as illustrated in FIG. 7A. That is, a deviation exists in the signal values in the right and left direction (X-axis direction) of the image. By using this fact, the right and left determination is performed from the signal deviation of the one-dimensional projection image in an x direction (FIG. 7B). Specifically, a threshold value $S_T$ is set to the signal value, and an average value $m_A$ (average value of positions) of positions (x) where signal values $S(x)$ becomes higher than the threshold value $S_T$ is calculated. For example, the threshold value $S_T$ is calculated by a method such as a discriminant analysis method. Alternatively, a median value between a maximum value and a minimum value may be simply set as the threshold value.

Next, a weighted average value $m_B$ (an average value of positions) of signal values of the position (x) where the signal intensity $S(x)$ is lower than the threshold value $S_T$ is calculated. It is assumed that weight wi is a standard value of the signal intensity $S(x)$ at each position x.

$$m_B = \Sigma(wi \times xi)/N$$

N: Total number of positions (x) where signal intensity $S(x)$ is lower than the threshold value $S_T$ $$wi = S(xi)/\{\Sigma S(xi)/N\}$$

Finally, the average values $m_A$ and $m_B$ are compared with each other. In the case of $m_A > m_B$, determination is made as the left shoulder, and in the case of $m_A < m_B$, determination is made as the right shoulder. In addition, a change may be made as follows. Specifically, a position where the signal value $S(x)$ takes an average value may be used instead of the average values $m_A$ and $m_B$, or a position where the signal value becomes a peak value may be used with respect to $m_A$. The imaging cross-section determination unit 200 may display the determination result on a display. According to this, in a case where a user cannot immediately determine the right and left from an image, from the display, the user can confirm which of the left and the right is imaged, and whether or not an examination protocol target is accurately set as an imaging target.

<S63: Feature Extraction>

After the right and left determination, the feature extraction unit 230 performs search for a characteristic structure and feature extraction with respect to a target site, here, the shoulder joint by using a first scout image (AX image). For example, it is assumed that a range of the search is set to a region where the signal value is determined to be higher than the threshold value in the right and left determination.

<<S63-1: Object Extraction>>

Figure 8:
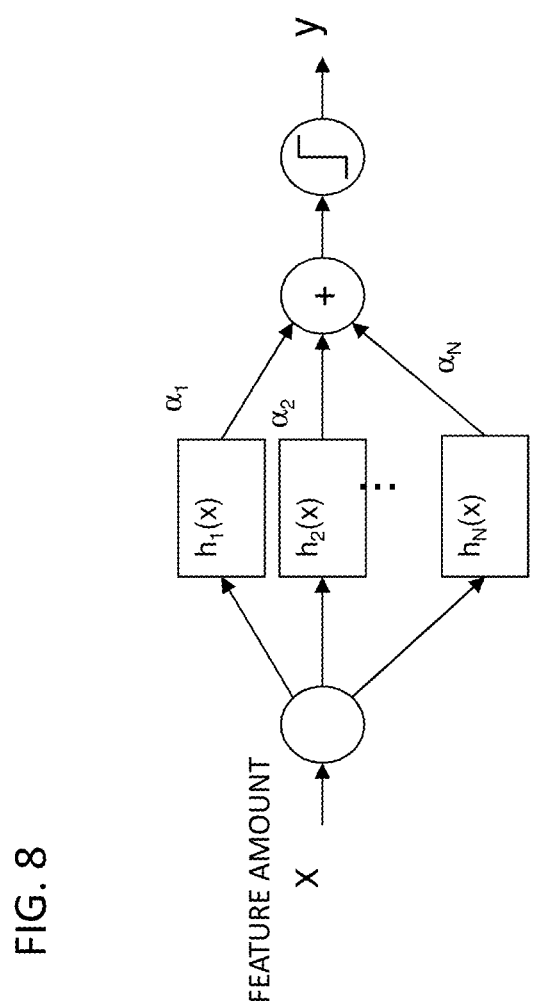
FIG. 8 is a view illustrating an algorithm of an adaptive boosting method as an example of an object extraction unit.

In this step, first, the object extraction unit 233 searches a joint plane of the humerus by using a known object extraction method such as adaptive boosting method. As illustrated in FIG. 8, the adaptive boosting method is one of object extraction methods using a relatively simple matching learning algorithm. In the adaptive boosting method, determination is made as to whether an answer is correct or not from a feature amount of input data x by respective discriminators h1(x) to hN(x), and final determination is made by weighted majority decision of a weak discriminator. In the course of learning, the weights α1 to αN of the respective discriminators which classify a correct answer and an incorrect answer with most accuracy are calculated by using input data x and output data y for which the correct answer and the incorrect answer are known in advance. In the case of desiring to extract a joint plane image of the humerus, a joint plane image is extracted from a plurality of images and is set as a correct answer data, and an image of another cross-section or an image of a humerus plane which is subjected to black painting or the like so that the feature of the humerus is lost is used as incorrect answer data. In addition, images having different angles such as images obtained by rotating an original image at an interval of 5° from −45° to 45° may be added as learning data.

Image data having the same size as the input data x used in the learning course of the mechanical learning algorithm is extracted from the search range of the AX image and is input to the learned mechanical learning algorithm as input data, and image data determined as a joint plane image of the humerus is extracted. According to this, a plurality of candidate images of the humerus joint plane are obtained.

<<S63-2: Matching>>

From the plurality of candidates of the humerus joint plane, the matching processing unit 231 calculates a position of an upper arm joint plane and an inclination of a line connecting a scapula and the humerus.

Figure 9A:
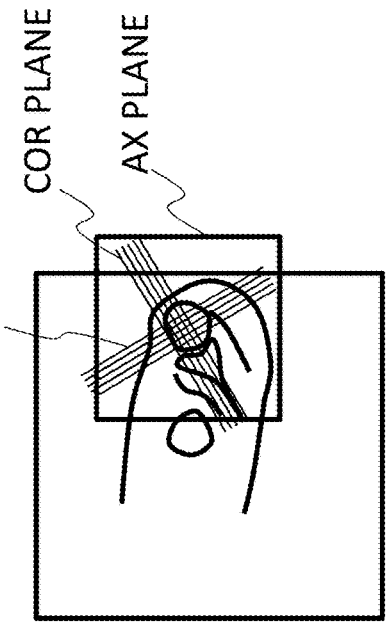
FIGS. 9A to 9C are views illustrating processing of a feature extraction unit with respect to the first scout image.
Figure 9C:
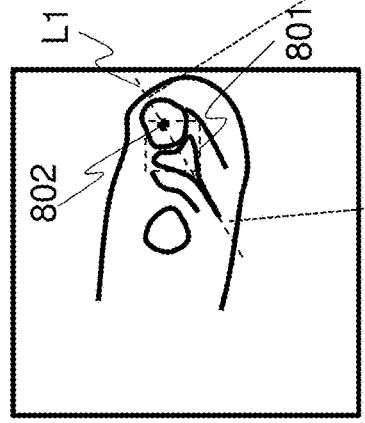
Figure 9B:
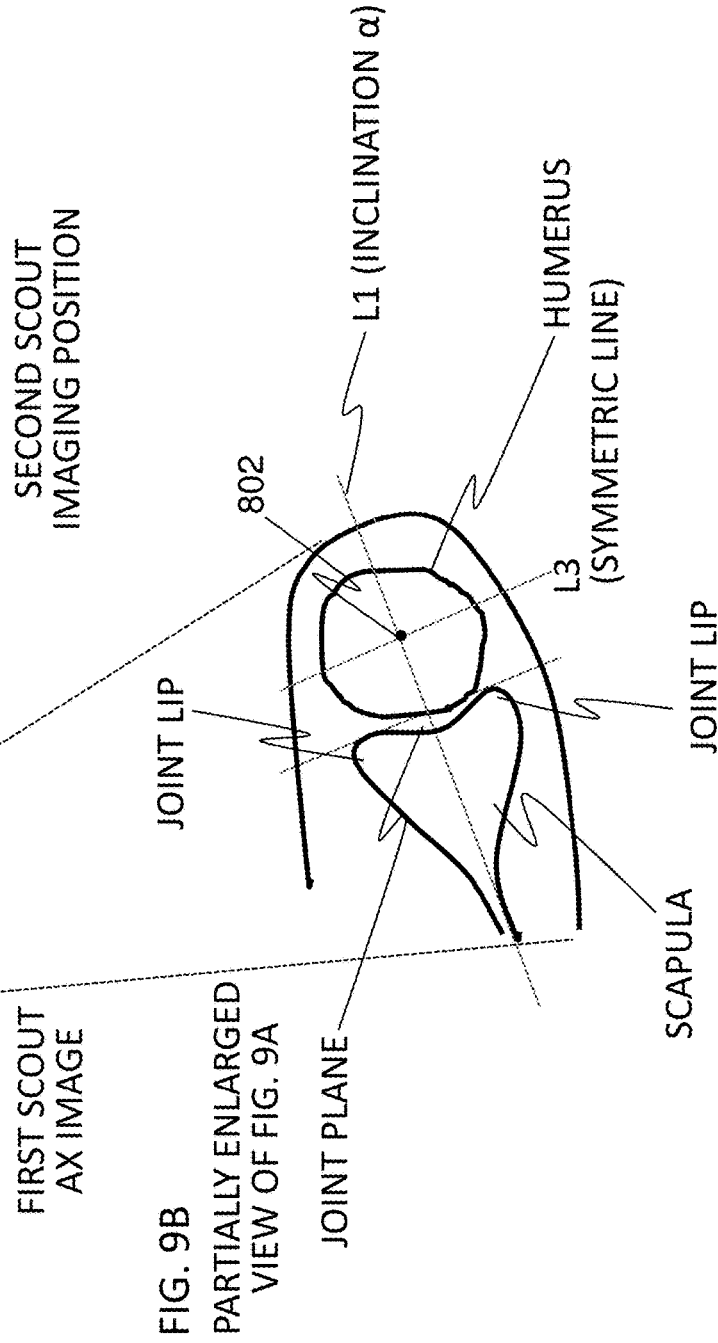

Specifically, positions of both ends (joint lip) of the scapula are specified through matching processing as illustrated in FIGS. 9A and 9B, and a region surrounding the both ends is set as a joint plane position 801. In addition, an inclination with respect to a template of line L1 connecting the scapula and the humerus is obtained.

<<S63-3: Symmetric Line Detection>>

In addition, the symmetric line detection unit 235 detects a symmetric line L3 that is orthogonal to the line L1 along the line L1 connecting the scapula and the humerus, and calculates a central position of the humerus.

Figure 10:
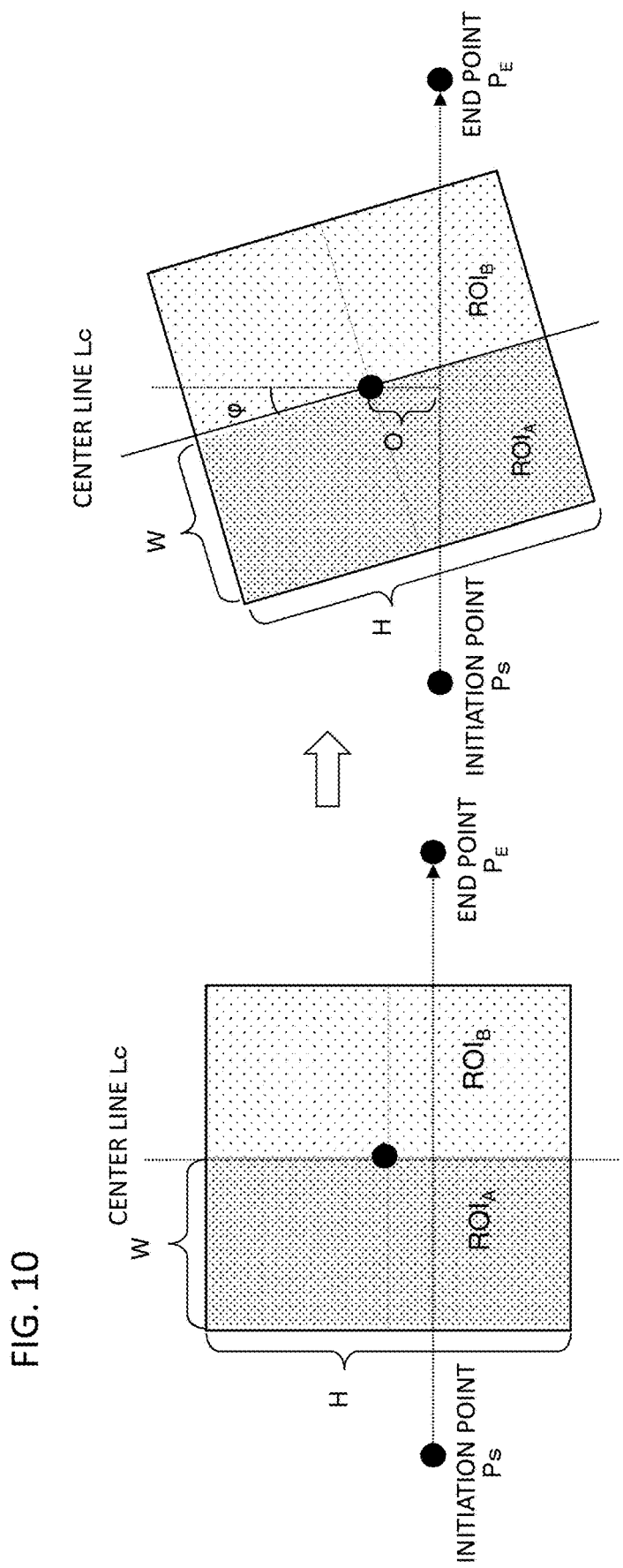
FIG. 10 is a view illustrating processing of a symmetric line detection unit.

The detection of the symmetric line can be performed by using the following method. First, with regard to an axial plane image, which is a target as illustrated in FIG. 10, regions $ROI_A$ and $ROI_B$ having a width W and a height H on both right and left sides of a center line Lc provided on the image are extracted, and the degree of matching between laterally inverted images of the $ROI_A$ and $ROI_B$ (or the degree of matching between laterally inverted images of $ROI_B$ and $ROI_A$). For example, calculation of the degree of matching can be performed by using a known method such as sum of squared difference (SSD) or sum of absolute difference (SAD). It is assumed that the size (W and H) of the ROI is preset in advance in correspondence with an examination target.

In such calculation of the degree of matching, a position of a center line at which the degree of matching is the highest is set as a symmetric line while changing positions where the $ROI_A$ and the $ROI_B$ are set within a predetermined search range. For example, in the case of extracting the symmetric line L3 in FIG. 9B, the search range is set to a predetermined range (a range from Ps to Pe) along the line L1, and with respect to a line connecting Ps and Pe at each position, a position providing an offset distance O is set as the center, and the degree of matching for every angle is obtained while changing an angle θ of a center line Lc. That is, the degree of matching is calculated while changing both the position of the center of the ROI and the angle of the center line, and a position and an angle at which the degree of matching becomes the maximum. It is assumed that the predetermined range and the offset distance are preset in advance in correspondence with a target site. A line determined at a position and an angle at which the degree of matching becomes the maximum through the search is set as the symmetric line L3. In the example in FIG. 9B, an intersection between the symmetric line L3 determined in this manner and the line L1 is set as a center position 802 of the humerus.

<S64: Cross-Section Position Calculation>

The cross-section position calculation unit 250 calculates a recommended imaging position in the second scout imaging on the basis of the position 801 of the humerus joint plane obtained in step S63 described above and the center position 802 of the humerus. Specifically, a recommended axial plane (AX plane) is calculated so that the center position 802 of the humerus becomes the center. In addition, a coronal plane (oblique COR plane) parallel to the line L1 connecting the scapula and the humerus, and a sagittal plane (oblique SAG plane) orthogonal to the coronal plane are set as a recommended imaging position in the second scout imaging. With regard to the oblique COR plane and the oblique SAG plane, a plurality of slice planes are set with a plane including the center position 802 of the humerus set as a center slice. An FOV of each cross-section or the number of slices are set according to imaging conditions set in advance.

<S65: Recommended Imaging Position Presentation>

The display control unit 330 displays the recommended cross-section determined by the imaging cross-section determination unit 200 on the display 111. A method of displaying the recommended cross-section is not particularly limited. For example, as illustrated in FIG. 9C, positions of a plurality of the COR planes parallel to the line L1 connecting the scapula and the humerus, positions of a plurality of the SAG planes orthogonal to the line L1 connecting the scapula and the humerus, and a position of the AX plane with the center position 802 of the humerus set as a center are presented on a first scout AX image as a second scout imaging position. A user confirms that there is no problem in the recommended imaging cross-section that is presented, and can proceed to the second scout imaging. In addition, the display control unit 330 may display a user interface such as a GUI that receives a user's adjustment in combination with display of the recommended imaging position, and in this case, the user can perform adjustment of the recommended imaging position through the user interface. Through steps S61 to S65 described above (FIG. 6A), automatic setting of the second scout imaging position is completed.

<S66: Second Scout Imaging>

The imaging control unit 310 receives an instruction for initiation of the second scout imaging from a user, and initiates the scout imaging. In the second scout imaging, the imaging unit 10 performs imaging at positions of respective imaging cross-sections (the AX plane, the oblique COR plane, and the oblique SAG plane) determined in step S64 described above, or the imaging cross-section position after position adjustment by the user, and acquires the scout image.

<S67, S68: Feature Extraction of Scout Image and Calculation of Imaging Cross-Section Position>

The imaging cross-section determination unit 200 performs calculation of an imaging cross-section position in the main imaging by using the images (the AX image, the oblique SAG image, and the oblique COR image) acquired in the second scout imaging. In this embodiment, with regard to the imaging cross-section position of the main imaging, three cross-sections are determined in such a manner the joint plane of the humerus is set as a center of an image, the AX plane becomes a plane orthogonal to a direction of the humerus, and in the SAG plane and the COR plane, a direction of the humerus becomes one axis (vertical axis) of an image.

<<S67-1: Processing Using AX Image>>

First, the AX image of the second scout imaging is set as an input, and as illustrated in FIG. 11A, a position 811 of the humerus joint plane is specified and an inclination α of a line L11 connecting the scapula and the humerus is calculated through matching processing as in a similar manner as in step S63-2. In addition, a symmetric line L33 orthogonal to the line L11 is extracted through symmetric line extraction processing, and a center 812 of the humerus which is an intersection between the line L11 and the symmetric line L33 is calculated. Information of the plane orthogonal to the line L11 and the center position 812 of the humerus is used as position information when creating an MPR image of the SAG plane in subsequent step S67-2.

<<S67-2: Processing Using SAG Image>>

Next, an MPR image as illustrated in FIG. 4 is created from the oblique SAG image including a plurality of pieces of slice data. The MPR image of the SAG plane uses the information obtained in step S67-1, and is set as a plane that passes through the center position of the humerus and is orthogonal to a line connecting the scapula and the humerus. According to this, an MPR image of the SAG as illustrated in FIG. 11B is created. In the MPR image, an inclination β of the humerus (inclination of the humerus on the MPR image) is also obtained. Processing of obtaining the inclination β of the humerus is similar to the symmetric line extraction processing described with reference to FIG. 10. That is, ROI ($ROI_A$ and ROIs) of which a size is determined in advance in conformity to a shape of the humerus is set on an image, and the degree of matching between an image in the ROI and a laterally inverted image thereof is calculated at each position and each angle while moving the ROI in a predetermined search range and changing an angle of the ROI at each position, and a position and an angle at which the degree of matching becomes the maximum are obtained. A center line of the two right and left $ROI_A$ and the ROIs at the position and the angle is set as a symmetric line, and an angle of the symmetric line is set as the inclination β of the humerus.

<<S67-3: Processing Using COR Image>>

Next, an MPR image is created from the oblique COR image obtained in the second scout imaging by using the angle J and the position of the symmetric line which are obtained in step S67-2 and the inclination α, which is calculated in step S67-1, of the line L11 connecting the scapula and the humerus. With regard to the MPR image, as in the MPR image of the SAG plane, an MPR image of a plane that passes through the joint plane center of the humerus and is parallel to the line L11 connecting the scapula and the humerus and the inclination β of the humerus is created as illustrated in FIG. 11C. The information of the inclination β of the humerus is obtained in the symmetric line extraction processing of the oblique SAG plane image described above. Next, a center position 813 and an inclination γ of the humerus joint plane in the COR plane are calculated from the created MPR image of the COR plane. The processing can be performed in a similar manner as in the symmetric line extraction processing described above. That is, a symmetric line is extracted with respect to the humerus, and an inclination in a direction orthogonal to the extracted symmetric line is set as the inclination γ of the humerus joint plane. Alternatively, the position and the inclination β of the humerus joint plane may also be calculated in matching processing.

<S68: Imaging Cross-Section Position Determination>

The cross-section position calculation unit 250 calculates imaging positions of the axial plane, the sagittal plane, and the coronal plane on the basis of the position 813 of the joint plane of the humerus and the inclinations (β and γ) of the humerus which are obtained in step S67-1 to step S67-3. Specifically, as illustrated in FIG. 12A, the imaging position of the axial plane becomes an oblique AX plane in which the humerus joint plane is set as a center of an image, which is inclined by an angle corresponding to the inclination β of the humerus in a direction orthogonal to the line L11 connecting the scapula and the humerus, and which is inclined by an angle corresponding to the inclination γ along a direction of the line L11 with the humerus center set as a center.

Similarly, the imaging positions of the sagittal plane and the coronal plane are an oblique SAG plane and an oblique COR plane which are orthogonal to the oblique AX plane described above and are orthogonal to each other, and become an oblique plane that is inclined along the axis of the humerus with the humerus joint plane set as a center as illustrated in FIGS. 12B and 12C.

<S69: Recommended Imaging Position Presentation>

The display control unit 330 causes a display device to display an imaging position of the main imaging which is determined by the above-described processing. With regard to a display example of the imaging position, for example, as illustrated in FIGS. 12A to 12C, the imaging position can be shown on the second AX plane scout image, the MPR image of the SAG plane, and the MPR image of the COR plane in a state of being surrounded by a rectangular frame line. A user can confirm a position or a range of an image to be acquired in the main imaging. In addition, the frame line may be set as a GUI that can be changed by the user, and according to this, the user can perform adjustment of the imaging position by changing the position or the size of the frame line.

In the case of receiving a change by the user (S70), the cross-section position calculation unit 250 may calculate again the imaging cross-section position that reflects the user's change, and the imaging cross-section position may be displayed on the display device 111 by the display control unit 330. Alternatively, the imaging position adjustment and execution unit 320 may receive the change by the user, and may change imaging parameters for determining the imaging position. The imaging control unit 310 initiates imaging at the imaging cross-section position that is finally determined.

As described above, according to this embodiment, after initiating the first scout imaging, the imaging cross-section position of the main imaging can be automatically determined. At this time, it is possible to collect information necessary or sufficient for determination of the imaging cross-section position without employing three-dimensional imaging in the first scout imaging and the second scout imaging, and thus it is possible to accomplish an automatic positioning function within shorter time in comparison to the related art.

Figure 13:
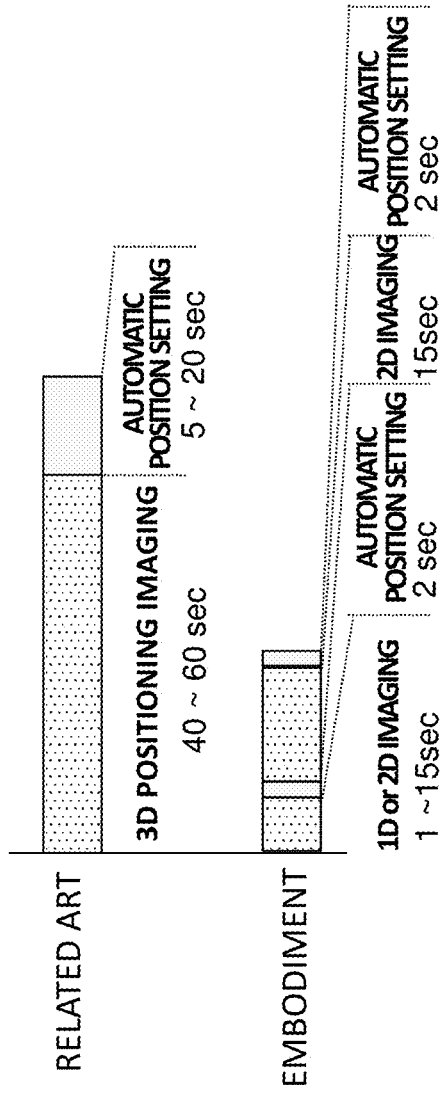
FIG. 13 is a view illustrating a difference in an effect between the first embodiment and the related art.

A time chart of time from the scout imaging to the automatic imaging cross-section position setting is illustrated in FIG. 13 while comparing a case where the related art is applied and a case where this embodiment is applied. As illustrated in the drawing, in the related art employing the three-dimensional imaging as the scout imaging, 40 to 60 seconds are taken for imaging, five or more seconds are taken for automatic position setting, and approximately 80 seconds are taken to the maximum. In contrast, according to this embodiment, it is possible to reduce both the imaging time and the computation time, and it is possible to complete the automatic position setting within approximately 34 seconds to the maximum.

In the above-described example, description has been given of an example in which the AX image, the SAG image, and the COR image are acquired in the second scout imaging, but the AX image can be imaged at the first scout imaging, and thus acquisition of the AX image may be omitted in the second imaging. According to this, it is possible to complete the automatic setting of the imaging position within shorter measurement time.

Second Embodiment

This embodiment is an embodiment of automatic positioning processing in a case where the examination site is a knee joint. Here, a cross-section position in the main imaging is determined in such a manner that a center position of a joint plane is set as a center of an image, the AX plane becomes a plane that is approximately orthogonal to a femur and a tibia, and the COR plane and the SAG plane become planes which are approximately parallel to the direction of the femur and the tibia.

Even in this embodiment a configuration of an apparatus is similar to the configuration as in the first embodiment, and description will be made with focus given to a configuration different from the first embodiment with reference to FIG. 14. FIG. 14 is a flowchart illustrating automatic positioning processing of this embodiment.

In this embodiment, description will be given of a case where the first scout imaging is one-dimensional measurement.

<S81 and S82: Right and Left Determination>

Under the control of the imaging control unit 310, after performing scout imaging that is the one-dimensional measurement (S81), the right and left determination unit 210 sets a one-dimensional projection image (for example, a graph as illustrated in FIG. 7B) as an input, and makes a determination as to whether an examination site is a right knee or a left knee (S82). In this embodiment, the one-dimensional data is obtained in the scout imaging, and thus projection processing is not necessary. In aright and left determination method, determination is made from intensity deviation of signal values in an x direction corresponding to a right and left axis as in the first embodiment.

<S83: Scout Imaging Position Determination of One Cross-Section>

The cross-section position calculation unit 250 determines a recommended imaging position (position of the AX plane) in the second scout imaging centered on either the left or the right on the basis of a determination result of the right and left determination unit 210 (S83). As the imaging position of the second scout imaging, for example, an AX plane, in which a position of an average value $m_A$ of positions x where signal intensity S(x) calculated from a one-dimensional profile is higher than a threshold value is set as a center of FOV, is set.

At this time, the determination result by the right and left determination unit 210 may be displayed on the display device 111 for user's confirmation. A presentation method may indicate either the left or the right, or the one-dimensional profile obtained in the first scout imaging and the determination result may be displayed. The user can confirm a situation in which the reception RF coil is correctly mounted with respect to an examination target of an examination protocol, or the like through the display.

<S84 to S86: Feature Extraction and Scout Imaging Position Determination of Another Cross-Section>

Figure 15A:
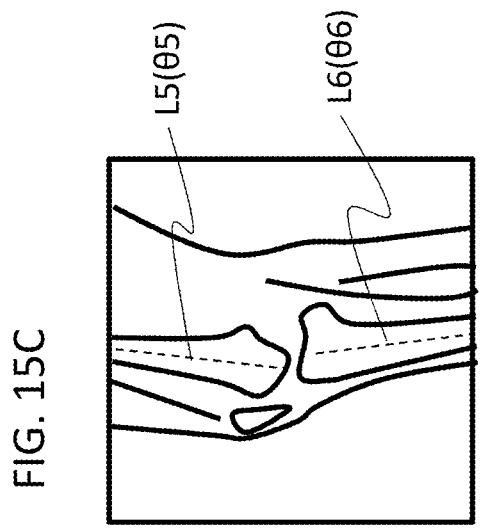
FIGS. 15A to 15C are views illustrating processing of the feature extraction unit with respect to the second scout image and the MPR image.

First, the imaging control unit 310 acquires an AX image (AX image of a plurality of slices), COR images (COR images of a plurality of slices) and SAG images (SAG images of a plurality of slices) orthogonal to each other at a position that is set (S84). To set the COR plane for main imaging, the AX image acquired in the scout imaging in step S82 is set as an input, and as illustrated in FIG. 15A, an inclination (θ4) of a line L4 connecting a medial condyle and a lateral condyle is calculated through matching processing (processing of the matching processing unit 231).

Figure 15B:
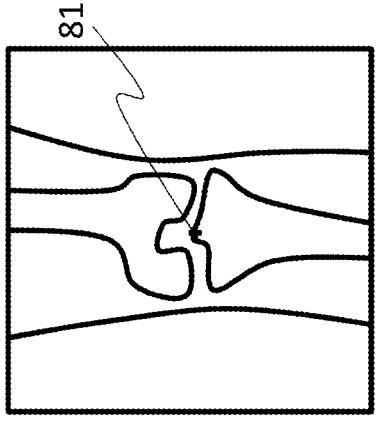

Next, feature extraction is performed by using a plurality of pieces of slice data acquired in the scout imaging of the COR plane (S85). First, MPR processing by the image cut-out unit 237 is performed with respect to the plurality of pieces of slice data of the COR plane, and an MPR image of a COR plane that passes through the line L4 connecting the medial condyle and the lateral condyle is created as illustrated in FIG. 15B. In the MPR image of the COR plane, a center position of a joint plane is obtained by the matching processing unit 231. A plane that passes through the center position and is orthogonal to the COR plane is set as an SAG plane.

Figure 15C:
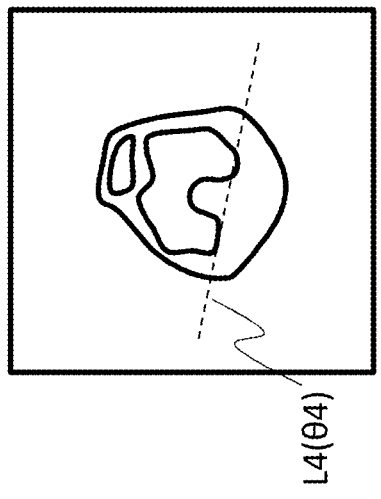

In addition, the MPR processing is performed with respect to a plurality of pieces of slice data of the SAG plane at the center position of the joint plane, and an MPR image of the SAG plane as illustrated in FIG. 15C is created, and performs feature extraction necessary for determination of an imaging cross-section position of the main imaging (S86). First, with regard to the created MPR image of the SAG plane image, the symmetric line detection unit 235 performs symmetric line extraction processing with respect to an upper portion and a lower portion of the joint plane, symmetric lines L5 and L6 are obtained, and inclinations thereof are calculated. The inclination of the upper symmetric line in the joint plane can be regarded as an inclination (θ5) of a femur, and the inclination of the symmetric line of the lower symmetric line in the joint plane can be regarded as an inclination (θ6) of a tibia.

<S87: Calculation of Cross-Section Position of Main Imaging, S88: Display>

The cross-section position calculation unit 250 calculates an imaging position of the main imaging by using the inclination (θ4), which is obtained in step S84, of the line L4 connecting the medial condyle and the lateral condyle, and the inclinations (θ5 and θ6), which are obtained in step S86, of the femur and the tibia, and presents the imaging position (S88). For example, each cross-section in the main imaging is set to so that the center position of the joint plane becomes a center position of an image. The AX plane is set in such a manner that the line L4 connecting the medial condyle and the lateral condyle and a horizontal axis of the image are parallel to each other, and the AX plane becomes a plane orthogonal to an average inclination of the inclination of the femur and the inclination of the tibia. The SAG plane is set in such a manner that a vertical axis of the image is parallel to the average inclination of the inclination of the femur and the inclination of the tibia, and the SAG plane becomes a plane orthogonal to a direction of the line L4 connecting the medial condyle and the lateral condyle. The COR plane is set to a plane that is parallel to the average of the inclination of the femur and the inclination of the tibia, and is parallel to the line L4 connecting the medial condyle and the lateral condyle.

A display example of the three cross-sections is illustrated in FIGS. 16A to 16C. In the example illustrated in the drawings, with respect to each of the three cross-sections, the AX image obtained in the scout imaging, the COR image subjected to the MPR processing, and the SAG image subjected to the MPR processing are displayed, and a position of each cross-section (bold-line square) is displayed in a state of being superimposed on each of the images. Even in this embodiment, a user's change can be accepted (S89).

According to this embodiment, since the right and left determination that becomes a premise at the time of the automatic positioning is performed by only the one-dimensional measurement, it is possible to greatly reduce time taken for scout imaging including the second scout imaging. In addition, since the second scout imaging is performed on the basis of the right and left determination result, it is possible to improve accuracy of feature extraction in an image obtained in the second scout imaging, and imaging position calculation based on the feature extraction.

In this embodiment, since determination on the right and left is performed with the one-dimensional imaging, scout imaging for confirming right and left positions is not necessary. One-dimensional imaging time is approximately one second, the scout imaging time of the three cross-sections is 10 to 15 seconds, and processing time is two seconds. Accordingly, the automatic positioning setting can be performed within 18 seconds to the maximum, and thus a time shortening effect is obtained in comparison to the related art in which the three-dimensional imaging is performed.

Hereinbefore, description has been given of embodiments in which the automatic positioning technology of the invention is applied to the shoulder joint and the knee joint. However, the invention is not limited to the sites, and is applicable to a site for which right and left determination is necessary, mainly, MRI examination of a joint, and the same effect can be obtained.

What is claimed is:
1. A magnetic resonance imaging apparatus comprising:
an imaging unit that acquires a cross-section image of a subject by using nuclear magnetic resonance;
an imaging control unit that performs control so that the imaging unit performs scout imaging for determining an imaging position, and main imaging for acquiring a diagnosis image; and
an imaging cross-section determination unit that determines an imaging cross-section position of the main imaging by using data acquired in the scout imaging,
wherein the imaging control unit performs control of executing first measurement for acquiring one-dimensional or two-dimensional measurement data and second measurement for acquiring two-dimensional measurement data as the scout imaging, wherein the imaging cross-section determination unit includes:
a right and left determination unit that determines the right and left of the subject by using the measurement data acquired in the first measurement; and
a cross-section position calculation unit that calculates a cross-section position for the second measurement by using a determination result in the right and left determination unit and the measurement data acquired in the first measurement, and calculates a cross-section position in the main imaging by using the measurement data acquired in the second measurement.

2. The magnetic resonance imaging apparatus according to claim 1,
wherein the right and left determination unit performs determination of the right and left on the basis of a signal value of the measurement data acquired in the first measurement in a one-dimensional direction along a right and left direction of the subject.

3. The magnetic resonance imaging apparatus according to claim 1,
wherein the imaging control unit performs control of acquiring two-dimensional measurement data in the first measurement, and
wherein the right and left determination unit creates one-dimensional data obtained by projecting the two-dimensional measurement data acquired in the first measurement in a one-dimensional direction along the right and left direction of the subject, and performs determination of the right and left by using the one-dimensional data.

4. The magnetic resonance imaging apparatus according to claim 3,
wherein the cross-section position calculation unit calculates a cross-section position in the second measurement with respect to a plurality of cross-sections including one cross-section by using measurement data of the one cross-section which is acquired in the first measurement.

5. The magnetic resonance imaging apparatus according to claim 1,
wherein the imaging control unit executes a pulse sequence in which a one-dimensional direction along the right and left direction of the subject is set as an echo signal read-out direction in the first measurement to perform control of acquiring the one-dimensional measurement data.

6. The magnetic resonance imaging apparatus according to claim 5,
wherein the cross-section position calculation unit calculates the cross-section position in the second measurement with respect to one cross-section on the basis of a result of right and left determination made by the right and left determination unit by using the one-dimensional measurement data acquired in the first measurement, and calculates the cross-section position in the second measurement with respect to cross-sections other than the one cross-section by using measurement data of the one cross-section which is acquired in the second measurement.

7. The magnetic resonance imaging apparatus according to claim 1,
wherein the imaging cross-section determination unit further includes a feature extraction unit that extracts a feature of an examination target tissue from the measurement data acquired in the first measurement or the second measurement.

8. The magnetic resonance imaging apparatus according to claim 7,
wherein the imaging cross-section determination unit further includes an image cut-out unit that cuts out a sheet of slice data including the examination target tissue from the measurement data that is acquired in the second measurement and corresponds to a plurality of slices, and creates an MPR (Multi-Planar Reconstruction) image, and
wherein the feature extraction unit extracts the feature of the examination target tissue from the MPR image created by the image cut-out unit.

9. The magnetic resonance imaging apparatus according to claim 7,
wherein the feature extraction unit includes a matching processing unit that calculates at least one of a position and an inclination of the examination target tissue as the feature of the examination target tissue by matching processing.

10. The magnetic resonance imaging apparatus according to claim 7,
wherein the feature extraction unit includes an object extraction unit that extracts a position of the examination target tissue from image data as the feature of the examination target tissue by using a mechanical learning algorithm.

11. The magnetic resonance imaging apparatus according to claim 7,
wherein the feature extraction unit includes a symmetric line detection unit that calculates a center line that is bilaterally symmetric with respect to the examination target tissue, and an inclination of the center line.

12. The magnetic resonance imaging apparatus according to claim 1, further comprising:
a display control unit that causes a display device to display the determination result of the right and left determination unit and/or the cross-section position calculated by the cross-section position calculation unit.

13. The magnetic resonance imaging apparatus according to claim 12,
wherein the display control unit includes a user interface that receives a user change relating to the cross-section position.

14. An automatic imaging position setting method of automatically setting an imaging cross-section position in imaging using a magnetic resonance imaging apparatus, the method comprising the steps of:
executing first measurement of scout imaging and acquiring one-dimensional or two-dimensional measurement data before main imaging for acquiring a diagnosis image;
determining the right and left of a subject by using measurement data acquired in the first measurement;
calculating a cross-section position for a second measurement of the scout imaging by using a determination result in the right and left determination and the measurement data acquired in the first measurement, executing the second measurement at the cross-section position, and acquiring two-dimensional measurement data; and
calculating a cross-section position in the main imaging by using the two-dimensional measurement data acquired in the second measurement.

15. The automatic imaging position setting method according to claim 14, wherein the two-dimensional measurement data is acquired in the first measurement, and one-dimensional data obtained by projecting the two-dimensional measurement data in a one-dimensional direction along a right and left direction of the subject is created, and wherein the right and left of the subject is determined on the basis of signal intensity of the one-dimensional data.

16. The automatic imaging position setting method according to claim 15, wherein cross-section positions of a plurality of cross-sections including one cross-section in the second measurement are calculated by using two-dimensional measurement data of the one cross-section which is acquired in the first measurement.

17. The automatic imaging position setting method according to claim 14, wherein the one-dimensional measurement data is acquired in the first measurement, and the right and left of the subject is determined on the basis of signal intensity of the one-dimensional data.

* * * * *